United States Patent
Ito

(10) Patent No.: US 11,369,447 B2
(45) Date of Patent: Jun. 28, 2022

(54) SURGICAL SYSTEM AND SUPPORT DEVICE

(71) Applicant: MEDICAROID CORPORATION, Kobe (JP)

(72) Inventor: Tetsushi Ito, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 94 days.

(21) Appl. No.: 16/745,203

(22) Filed: Jan. 16, 2020

(65) Prior Publication Data

US 2020/0229882 A1 Jul. 23, 2020

(30) Foreign Application Priority Data

Jan. 21, 2019 (JP) .............................. JP2019-007600

(51) Int. Cl.
| | |
|---|---|
| *A61B 34/37* | (2016.01) |
| *A61B 34/30* | (2016.01) |
| *A61B 17/068* | (2006.01) |
| *A61B 17/08* | (2006.01) |
| *A61B 17/29* | (2006.01) |

(Continued)

(52) U.S. Cl.
CPC ............ *A61B 34/37* (2016.02); *A61B 17/068* (2013.01); *A61B 17/08* (2013.01); *A61B 17/29* (2013.01); *A61B 17/3201* (2013.01); *A61B 2017/00398* (2013.01); *A61B 2018/1412* (2013.01); *A61B 2034/301* (2016.02)

(58) Field of Classification Search
CPC . A61B 34/37; A61B 2034/301; A61B 17/068; A61B 17/08; A61B 17/29; A61B 17/3201; A61B 2017/00398; A61B 2018/1412; A61B 2017/3445; A61B 2017/348; A61B 17/3415; A61B 2017/00477; A61B 46/10; A61B 90/50
See application file for complete search history.

(56) References Cited

U.S. PATENT DOCUMENTS

| | | | |
|---|---|---|---|
| 8,746,252 B2 | 6/2014 | McGrogan et al. | |
| 8,784,435 B2 | 7/2014 | Cooper et al. | |

(Continued)

FOREIGN PATENT DOCUMENTS

| | | | | |
|---|---|---|---|---|
| EP | 3388016 A1 | * | 10/2018 | ............. A61B 34/70 |
| EP | 3388016 A1 | | 10/2018 | |

(Continued)

*Primary Examiner* — Joseph M Dietrich
*Assistant Examiner* — Michael T. Holtzclaw
(74) *Attorney, Agent, or Firm* — Metrolex IP Law Group, PLLC

(57) ABSTRACT

A surgical system according to one or more embodiments may include: a plurality of surgical instruments each including a flexible shaft and an end effector; an insertion tube to hold the plurality of flexible shafts and to be inserted into a body of a patient from one end of the insertion tube; and a support device for supporting the plurality of surgical instruments and the insertion tube. The support device includes a plurality of supports respectively supporting the plurality of surgical instruments, a support mechanism supporting the plurality of supports together, and an insertion tube holder holding the insertion tube. The plurality of supports independently and movably support the plurality of surgical instruments, respectively.

18 Claims, 5 Drawing Sheets

(51) Int. Cl.
  *A61B 17/3201* (2006.01)
  *A61B 17/00* (2006.01)
  *A61B 18/14* (2006.01)

(56) References Cited

U.S. PATENT DOCUMENTS

| | | | |
|---|---|---|---|
| 8,852,208 B2 | 10/2014 | Gomez et al. | |
| 8,945,148 B2 | 2/2015 | Solomon et al. | |
| 9,096,033 B2 | 8/2015 | Holop et al. | |
| 9,301,807 B2 | 4/2016 | Duval | |
| 9,757,149 B2 | 9/2017 | Cooper et al. | |
| 9,801,654 B2 | 10/2017 | Gomez et al. | |
| 9,955,996 B2 | 5/2018 | Solomon et al. | |
| 2008/0243064 A1* | 10/2008 | Stabler | A61B 34/30 604/95.01 |
| 2011/0071544 A1 | 3/2011 | Steger et al. | |
| 2011/0277775 A1 | 11/2011 | Holop et al. | |
| 2011/0282358 A1* | 11/2011 | Gomez | B32B 3/12 606/130 |
| 2016/0184030 A1* | 6/2016 | Seeber | B25J 18/007 606/130 |
| 2017/0072561 A1* | 3/2017 | Schlegel | B25J 9/1035 |
| 2018/0200895 A1 | 7/2018 | Kan | |
| 2018/0214220 A1* | 8/2018 | Kan | B25J 17/0241 |
| 2018/0214226 A1 | 8/2018 | Kan | |
| 2018/0370045 A1 | 12/2018 | Kan | |
| 2019/0159852 A1 | 5/2019 | Ito et al. | |
| 2019/0159854 A1 | 5/2019 | Ito | |
| 2019/0201149 A1 | 7/2019 | Ito et al. | |

FOREIGN PATENT DOCUMENTS

| | | |
|---|---|---|
| JP | 2013-526337 A | 6/2013 |
| WO | 2017/006375 A1 | 1/2017 |
| WO | 2018/174226 A1 | 9/2018 |
| WO | 2018/174227 A1 | 9/2018 |
| WO | 2018/174228 A1 | 9/2018 |

\* cited by examiner

SURGICAL SYSTEM AND SUPPORT DEVICE

CROSS REFERENCE TO RELATED APPLICATIONS

This application claims priority to Japanese Patent Application No. 2019-007600 filed on Jan. 21, 2019, the entire contents of which are incorporated herein by reference.

BACKGROUND

One or more embodiments may relate to a surgical system and a support device, and more particularly, to a surgical system including a plurality of surgical instruments, and a support device for supporting a plurality of surgical instruments.

Surgical systems including a plurality of surgical instruments have been known (see, for example, Japanese Translation of PCT International Application Publication No. 2013-526337).

Japanese Translation of PCT International Application Publication No. 2013-526337 discloses a surgical system including a plurality of surgical instruments, an arm assembly that supports the plurality of surgical instruments together, and a cart having a support post that supports the arm assembly. According to the surgical system of Japanese Translation of PCT International Application Publication No. 2013-526337, each of the plurality of surgical instruments has an elongated rigid shaft, and a main body for driving an end effector attached to a distal end of the rigid shaft. The plurality of surgical instruments are configured to be moved together by the arm assembly, which is a support device.

SUMMARY

According to the surgical system described in Japanese Translation of PCT International Application Publication No. 2013-526337, the plurality of elongated rigid shafts are inserted into a single cannula to insert the plurality of surgical instruments into a patient's body. Therefore, the main bodies of the surgical instruments may need to be arranged adjacent to each other. This may involve a problem in that the surgical instruments cannot be arranged apart from each other on the support device, which decreases the degree of freedom in the arrangement of the surgical instruments. Further, in the surgical system described in Japanese Translation of PCT International Application Publication No. 2013-526337, the plurality of surgical instruments each having the elongated rigid shaft may be moved together. Thus, a large support device having the arm assembly and the support post for supporting the arm assembly is used. Thus, the surgical system described in Japanese Translation of PCT International Application Publication No. 2013-526337 may have a problem in that the large support device increases the cost.

An object of one or more embodiments may be to provide a surgical system and a support device capable of improving the degree of freedom in the arrangement of a plurality of surgical instruments. Another object of one or more embodiments may be to provide a surgical system and a support device capable of reducing the size of a support device that supports a plurality of surgical instruments.

A first aspect of one or more embodiments may be a surgical system that may include: a first surgical instrument including a first flexible shaft and a first end effector; a second surgical instrument including a second flexible shaft and a second end effector; a third surgical instrument including a third flexible shaft and a third end effector; a fourth surgical instrument including a fourth flexible shaft and a fourth end effector; an insertion tube that holds the first flexible shaft, the second flexible shaft, the third flexible shaft, and the fourth flexible shaft, to be inserted into a body of a patient from one end of the insertion tube; and a support device, wherein the support device may include: a first support supporting the first surgical instrument movably; a second support provided independently of the first support and supporting the second surgical instrument movably; a third support provided independently of the first support and the second support and supporting the third surgical instrument movably; a fourth support provided independently of the first support, the second support, and the third support and supporting the fourth surgical instrument movably; a support mechanism supporting the first support, the second support, the third support, and the fourth support so as to be movable together; and an insertion tube holder holding the insertion tube, wherein the first support, the second support, the third support, and the fourth support independently and movably support the first surgical instrument, the second surgical instrument, the third surgical instrument, and the fourth surgical instrument independently, respectively.

A second aspect of one or more embodiments may be directed to a support device for supporting first to fourth surgical instruments. The support device may include: a first support movably supporting the first surgical instrument including a first flexible shaft and a first end effector; a second support movably supporting the second surgical instrument including a second flexible shaft and a second end effector; a third support movably supporting the third surgical instrument including a third flexible shaft and a third end effector; a fourth support movably supporting the fourth surgical instrument including a fourth flexible shaft and a fourth end effector; a support mechanism supporting the first support, the second support, the third support, and the fourth support so as to be movable together; and an insertion tube holder holding an insertion tube to hold the first to fourth flexible shafts, wherein the first support, the second support, the third support, and the fourth support independently and movably support the first surgical instrument, the second surgical instrument, the third surgical instrument, and the fourth surgical instrument independently, respectively.

DETAILED DESCRIPTION

One or more embodiments will be described below with reference to the drawings.

(Configuration of Surgical System)

Figure 1:
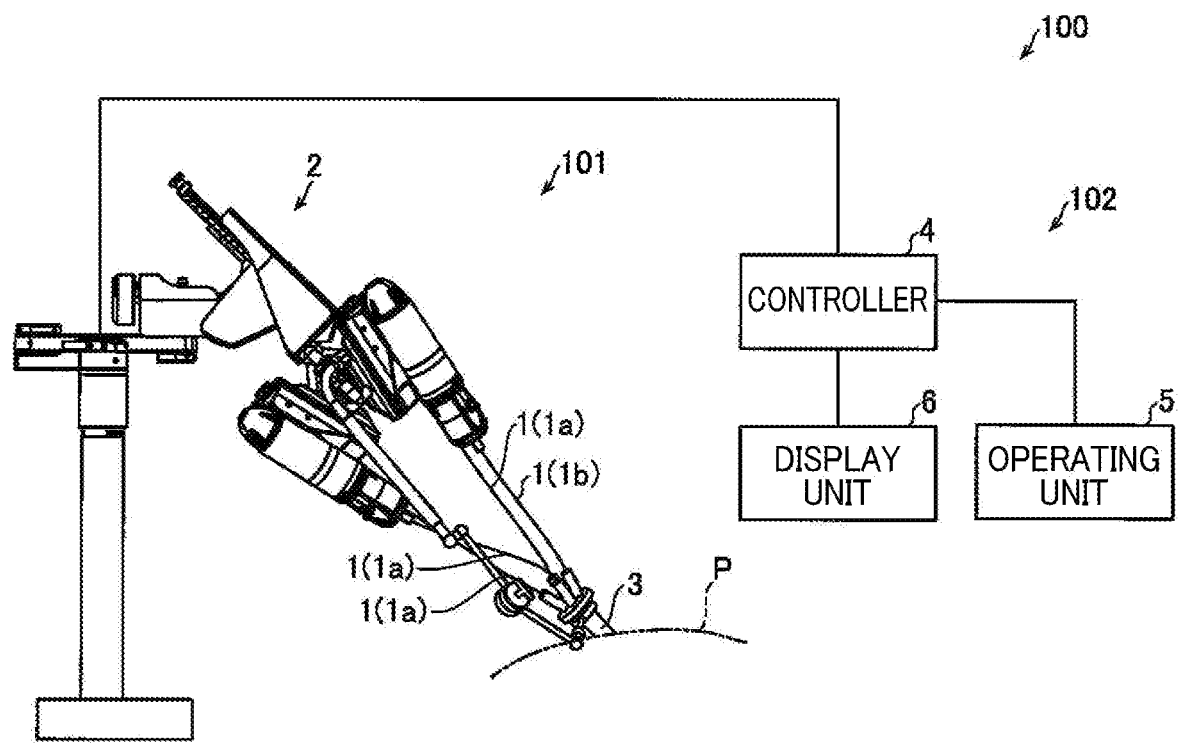
FIG. 1 is a diagram schematically illustrating a surgical system according to an embodiment.

Referring to FIG. 1, a configuration of a surgical system 100 according to an embodiment will be described below.

As shown in FIG. 1, the surgical system 100 includes a patient-side apparatus 101 and a remote control apparatus 102. The remote control apparatus 102 is used to remotely control medical equipment provided for the patient-side apparatus 101. When an operator, who is a surgeon, enters a movement type instruction to be executed by the patient-side apparatus 101 to the remote control apparatus 102, the remote control apparatus 102 transmits the movement type instruction to the patient-side apparatus 101. The patient-side apparatus 101 then handles the medical equipment, such as a surgical instrument 1a or an endoscope 1b attached to a support device 2, in response to the movement type instruction transmitted from the remote control apparatus 102. A minimally invasive operation is performed in this manner.

The patient-side apparatus 101 includes a plurality of surgical instruments 1, a support device 2, and an insertion tube 3. The remote control apparatus 102 includes a controller 4, an operating unit 5, and a display unit 6. The surgical instruments 1 include three surgical instruments 1a that perform treatment on a surgical region, and a single endoscope 1b that photographs the surgical region. The surgical instrument 1a is an example of a "first surgical instrument," a "second surgical instrument," and a "third surgical instrument" recited in the claims. The endoscope 1b is an example of a "fourth surgical instrument" and a "flexible endoscope" recited in the claims.

The support device 2 supports the surgical instruments 1 (the surgical instruments 1a and the endoscope 1b) and the insertion tube 3. The support device 2 is arranged in the vicinity of a treatment table on which a patient P lies. For example, the support device 2 may be attached to the treatment table. The support device 2 may be arranged in the vicinity of the treatment table independently of the treatment table.

The remote control apparatus 102 and the patient-side apparatus 101 constitute a master-slave system in controlling the movements. Specifically, the operating unit 5 serves as a controlling element (i.e., a master) in the master-slave system, and the patient-side apparatus 101 to which the medical equipment is attached serves as a moving element (i.e., a slave). When the operator operates the operating unit 5, the movement of the patient-side apparatus 101 is controlled so that the distal end portion of the surgical instrument 1 will trace the movement of the operating unit 5.

The display unit 6 is configured to display the image captured by the endoscope 1b and information related to the surgery. The controller 4 is configured to control the movement of the patient-side apparatus 101 based on the operation by the operating unit 5.

(Configuration of Surgical Instrument)

Figure 2:
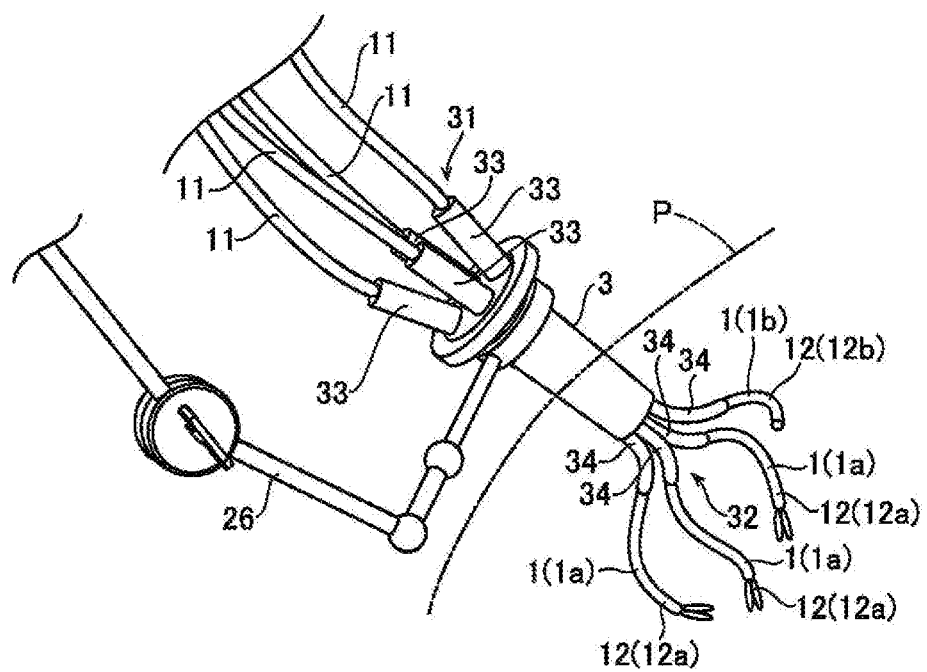
FIG. 2 is a diagram illustrating a plurality of surgical instruments and insertion tube of the surgical system according to an embodiment.

As shown in FIG. 2, the plurality of surgical instruments 1 (the surgical instruments 1a and the endoscope 1b), held by the insertion tube 3, is inserted into the body of the patient P. FIG. 2 shows a state where the plurality of surgical instruments 1 (the surgical instruments 1a and the endoscope 1b) and the insertion tube 3 are inserted into the body of the patient P.

Each of the surgical instruments 1 (the surgical instruments 1a and the endoscope 1b) has an elongated flexible shaft 11, and an end effector 12 arranged at a distal end of the flexible shaft 11. Examples of an end effector 12a of the surgical instrument 1a include treatment tools such as a grasping forceps, scissors, a hook, a high-frequency knife, a snare wire, a clamp, and a stapler. The end effector 12a of the surgical instrument 1a is not limited to these tools and may include various types of treatment tools. Examples of an end effector 12b of the endoscope 1b include a camera and an illuminator. The endoscope 1b is, for example, a flexible endoscope. The flexible shaft 11 is an example of a "first flexible shaft," a "second flexible shaft," a "third flexible shaft," and a "fourth flexible shaft" recited in the claims. The end effector 12a is an example of a "first end effector," a "second end effector," and a "third end effector" recited in the claims. The end effector 12b is an example of a "fourth end effector" recited in the claims.

The insertion tube 3 is configured to hold the plurality of flexible shafts 11. The flexible shafts 11 are made of soft plastic such as polypropylene and vinyl chloride. Each flexible shaft 11 has an elongated hollow cylindrical shape. The insertion tube 3 is inserted into the body of the patient P from one end of the insertion tube 3. Specifically, the insertion tube 3 is flexible and is made of soft plastic such as polypropylene and vinyl chloride. The insertion tube 3 has a first end 31 and a second end 32. Further, the insertion tube 3 is configured to allow the end effectors 12 (12a, 12b) to be inserted into the insertion tube 3 from the first end 31 and introduced into the body of the patient P from the second end 32. Thus, the insertion tube 3 can collectively guide the end effectors 12 (12a, 12b) of the plurality of surgical instruments 1 into the body of the patient P.

The insertion tube 3 includes four guide tubes 33 and four guide tubes 34 which are respectively connected to the four guide tubes 33. The guide tubes 33 and 34 are made of soft plastic such as polypropylene and vinyl chloride. That is, the guide tubes 33 and 34 are configured to be bendable. Each of the guide tubes 33 and 34 guides the end effector 12 of an associated one of the surgical instruments 1 into the body of the patient P. Further, the guide tubes 34 can be kept bent. Thus, the end effectors 12 can be spaced apart from each other.

The insertion tube 3, when used in a laparoscopic surgery, for example, is inserted into the body cavity of the patient from an incision formed in the body surface of the patient P. Instead of being inserted from the incision, the insertion tube 3 may be inserted into the patient's body from a natural orifice, such as an oral cavity.

The insertion tube 3 is held by, for example, an insertion tube holder 27 of the support device 2. Thus, the position and orientation of the insertion tube 3 are fixed.

Figure 3:
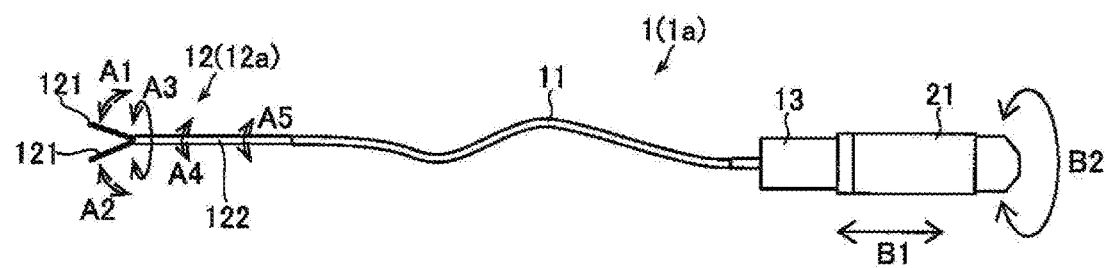
FIG. 3 is a diagram illustrating the surgical instrument of the surgical system according to an embodiment.

As shown in FIG. 3, the surgical instrument 1 includes the flexible shaft 11, the end effector 12, and a main body 13. The end effector 12 includes a pair of jaws 121 and a multi-articulated portion 122. FIG. 3 shows an example in which the end effector 12 is a grasping forceps, but the end effector 12 may be a tool other than the grasping forceps. The flexible shaft 11 is configured to be bendable.

A wire is connected to each of the pair of jaws 121 so that the jaw is driven to open and close by the wire. The jaws 121 are driven to open and close in the directions of arrows A1 and the directions of arrows A2, respectively. The pair of jaws 121 are configured to be rotated in the directions of arrows A3 by the rotation of a torque transmission tube disposed in the flexible shaft 11. The multi-articulated portion 122 is configured to bend in the directions of arrows A4 and A5 by a wire. Thus, the positions of the distal ends of the plurality of end effectors 12 can be easily adjusted by the multi-articulated portions 122. The wires transmitting the driving force are connected to the main body 13.

(Configuration of Support Device)

Figure 4:
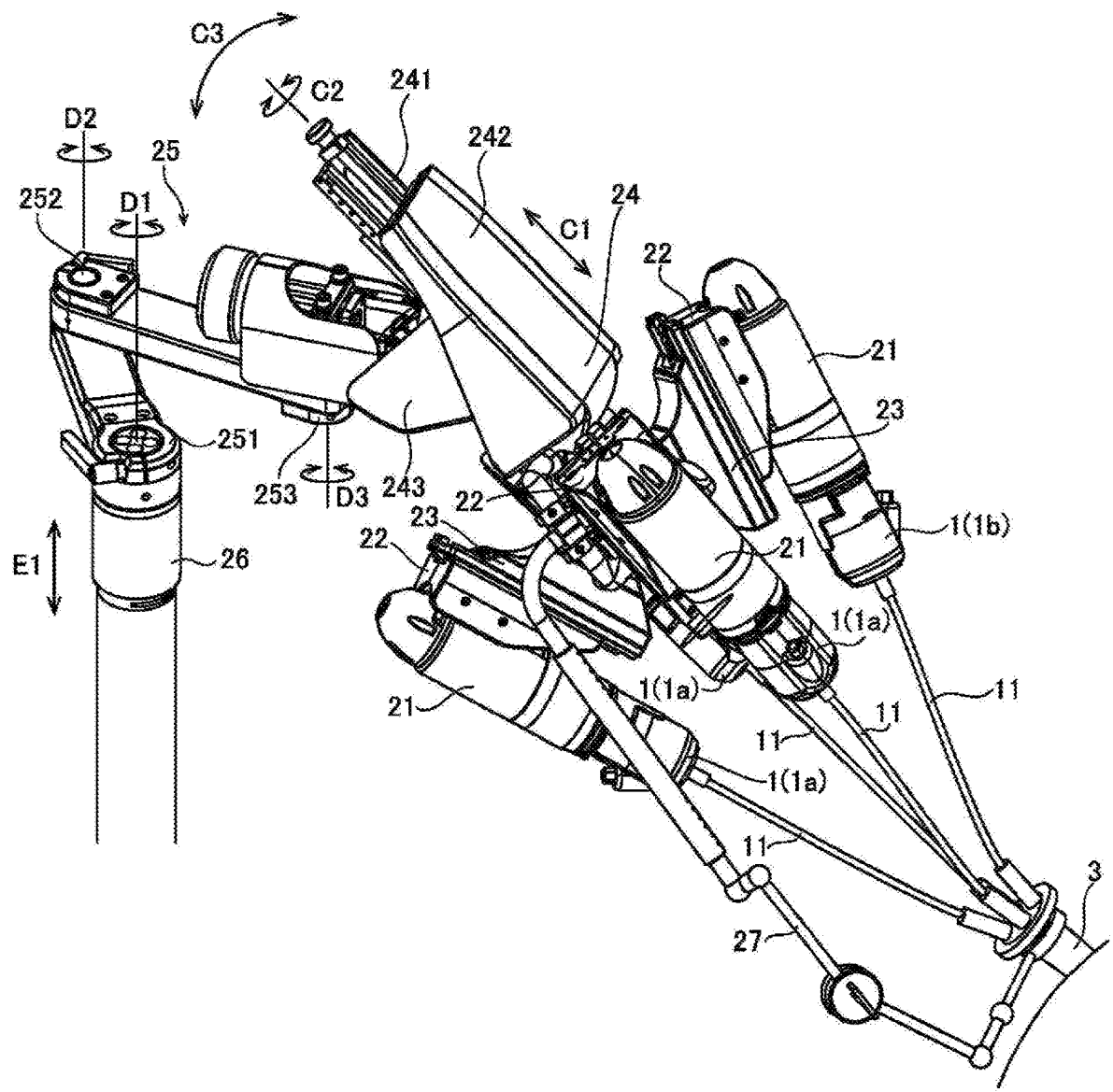
FIG. 4 is a diagram illustrating a support device of the surgical system according to an embodiment.

As shown in FIG. 4, the support device 2 includes a plurality of holders 22, a plurality of supports 23, and a support mechanism 24. Each of the holders 22 holds a driving section 21 for driving an associated one of the surgical instruments 1 (the surgical instruments 1a and the endoscope 1b). Each of the supports 23 supports an associated one of the holders 22. The support mechanism 24 is configured to support the plurality of supports 23 together. In this configuration, the surgical instruments 1 are independently movable by being supported by the respective supports 23 independently arranged via the respective holders 22, and the support mechanism 24 can move the surgical instruments 1 together. Thus, the positions of the plurality of surgical instruments relative to the insertion tube and the surgical field can be easily adjusted. Further, since each of the surgical instruments 1 has the flexible shaft 11, the supports 23 can be arranged apart from, and independently of, each other. This can increase the degree of freedom in the arrangement of the plurality of surgical instruments 1 in the support device.

The support device 2 further includes an insertion tube holder 27 that holds the insertion tube 3. The support device 2 also includes a vertical movement mechanism 26 for moving the support mechanism 24 in a vertical direction, and a horizontal movement mechanism 25 for moving the support mechanism 24 in a horizontal direction. The vertical movement mechanism 26 can easily change the vertical position of the support mechanism 24, and the horizontal movement mechanism 25 can easily change the horizontal position of the support mechanism 24.

Four driving sections 21 are provided. In other words, each of the four driving sections 21 is configured to drive an associated one of the four surgical instruments 1. The surgical instruments 1 (the surgical instruments 1a and the endoscope 1b) are configured to be attachable to and detachable from the four driving sections 21, respectively. Accordingly, the surgical instruments 1 can be replaced depending on the situation, which allows the surgical system to address various kinds of operation.

Figure 6:
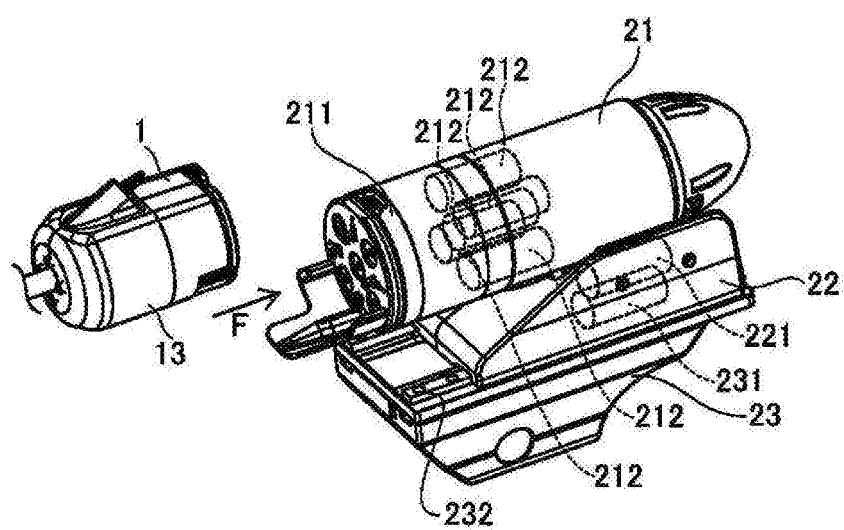
FIG. 6 a diagram illustrating a state where the surgical instrument of the surgical system according to an embodiment is not attached to the holder.

As shown in FIG. 6, each driving section 21 includes five motors 212. The driving section 21 is configured to transmit a driving force to the corresponding surgical instrument 1 via a drape adapter 211. Specifically, the driving force of the driving section 21 is transmitted to the main body 13 of the surgical instrument 1 and is transmitted to the end effector 12 via a wire or a gear disposed in the main body 13. Note that the main body 13 is an example of a "first main body," a "second main body," a "third main body," and a "fourth main body" recited in the claims.

The holders 22 are provided independently of each other. Further, the holders 22 respectively hold the driving sections 21. Specifically, as shown in FIG. 3, each holder 22 is configured to rotate the driving section 21 about a rotation axis parallel to the longitudinal direction of the surgical instrument 1. That is, the holder 22 holds the entire surgical instrument 1 so as to be rotatable in the directions of arrows B2. Since the surgical instruments 1 can be independently rotated about the rotation axis parallel to the longitudinal direction of the surgical instrument 1, the rotational position of the end effectors 12 of the surgical instruments 1 can be independently adjusted. Specifically, as shown in FIG. 6, the holder 22 includes a motor 221. The motor 221, when driven, rotates the driving section 21 in the directions of arrows B2.

The supports 23 are provided to be independent of, and apart from, each other and respectively support the holders 22. Specifically, as shown in FIG. 3, each support 23 is configured to translate (e.g. linearly move) the holder 22 in the longitudinal direction of the surgical instrument 1. That is, the support 23 supports the entire surgical instrument 1 so as to be capable of translating in the directions of arrows B1. Since the surgical instruments 1 can independently translate in the longitudinal direction of the surgical instruments 1, the positions of the end effectors 12 of the surgical instruments 1 can be independently adjusted. Specifically, as shown in FIG. 6, the support 23 includes a motor 231. The motor 231, when driven, translates the holder 22 in the directions of arrows B1. The support 23 further includes a guide 232 for guiding the translational movement of the holder 22. The guide 232 includes a pair of rails formed to extend along the directions of arrows B1.

Figure 7:
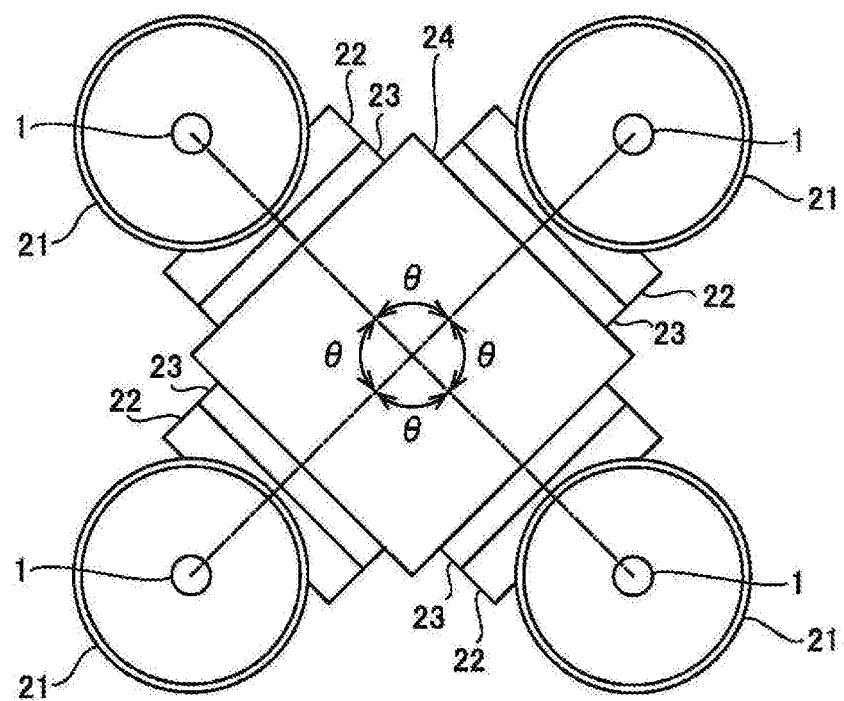
FIG. 7 a diagram illustrating a plurality of supports of the support device of the surgical system according to an embodiment.

As shown in FIG. 7, the support mechanism 24 supports the four supports 23 so as to be arranged at regular intervals in a circumferential direction about a center line. Specifically, the support mechanism 24 supports the four supports 23 at an interval of an angle θ (about 90 degrees). Thus, the support mechanism 24 can hold the four surgical instruments 1 in a balanced state.

As shown in FIG. 4, the support device 2 includes a translation mechanism 241 configured to collectively translate the four supports 23 along the center line by translating the support mechanism 24. The translation mechanism 241 is configured to be capable of translating the four supports 23 together in the directions of arrows C1. Thus, the translation mechanism 241 can translate the plurality of surgical instruments 1 together.

The support device 2 also includes a rotation mechanism 242 configured to rotate the support mechanism 24 about the center line. The rotation mechanism 242 is configured to be capable of rotating the four supports 23 together in the directions of arrows C2. Thus, the rotation mechanism 242 can rotate the plurality of surgical instruments 1 together.

Further, the support device 2 also includes an angle change mechanism 243 which rotates the support mechanism 24 to collectively change the angles of the four supports 23 relative to a horizontal plane. The angle change mechanism 243 is configured to be capable of rotating the four supports 23 together in the directions of arrows C3. Thus, the angle change mechanism 243 can collectively change the angles of the plurality of surgical instruments 1 relative to the horizontal plane.

The horizontal movement mechanism 25 has joints 251, 252, and 253. Each of the joints 251, 252, and 253 is configured to be rotatable about a vertical rotation axis. The joint 251 rotates in the directions of arrows D1. The joint 252 rotates in the directions of arrows D2. The joint 253 rotates in the directions of arrows D3. That is, the horizontal movement mechanism 25 has three degrees of freedom.

The vertical movement mechanism 26 is configured to be able to collectively move the four supports 23 by moving the support mechanism 24 in the directions of arrows E1 with a ball screw. That is, the support device 2 is configured to be able to move the support mechanism 24 in seven directions, i.e., the directions of arrows C1, C2, C3, D1, D2, D3, and E1.

The insertion tube holder 27 supports the insertion tube 3 to fix the position and orientation of the insertion tube 3. The insertion tube holder 27 is connected to the support mechanism 24. The insertion tube holder 27 has a plurality of joints and can support the insertion tube 3 while adjusting the position and orientation of the insertion tube 3.

Figure 5:
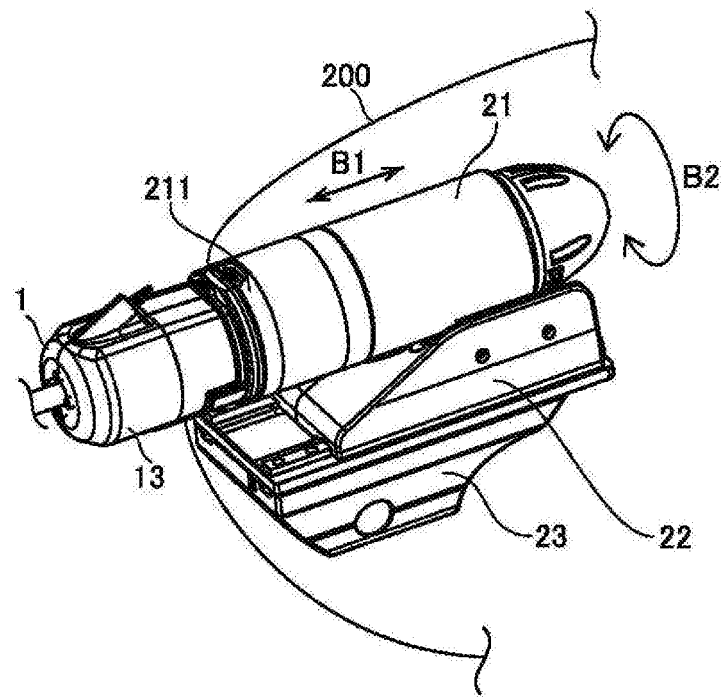
FIG. 5 is a diagram illustrating a state where the surgical instrument of the surgical system according to an embodiment is attached to a holder.

As shown in FIG. 5, each of the plurality of surgical instruments 1 is configured to be attachable to and detachable from the driving section 21 via the drape adapter 211. Thus, the plurality of surgical instruments 1 can be easily attached to the support mechanism 24 covered with a drape 200. The drape 200 is placed to cover the support mechanism 24 holding the four surgical instruments 1. The drape 200 is configured to cover the entire support device 2. The drape 200 may be provided for each of the four surgical instruments 1 so as to cover an associated one of the driving sections 21.

The drape 200 is arranged between the support device 2 and the surgical instrument 1. Specifically, the drape 200 is arranged between the drape adapter 211 and the support device 2 (driving section 21). The drape adapter 211 is attached to the support device 2 with the drape 200 sandwiched therebetween. The surgical instrument 1 is attached to the drape adapter 211 attached to the support device 2 with the drape 200 interposed therebetween.

As shown in FIG. 6, the surgical instrument 1 is moved along the direction of extension of the flexible shaft 11 and is thereby attached to the driving section 21. Specifically, the surgical instrument 1 is moved in the direction of an arrow F to be attached to the driving section 21. The surgical instrument 1, when attached to the driving section 21, engages with the driving section 21 so that the driving forces from the five motors 212 are independently transmitted. The surgical instrument 1 is detached from the driving section 21 when it is moved along the direction of extension of the flexible shaft 11.

(Configuration of Surgical Instrument)

Figure 8:
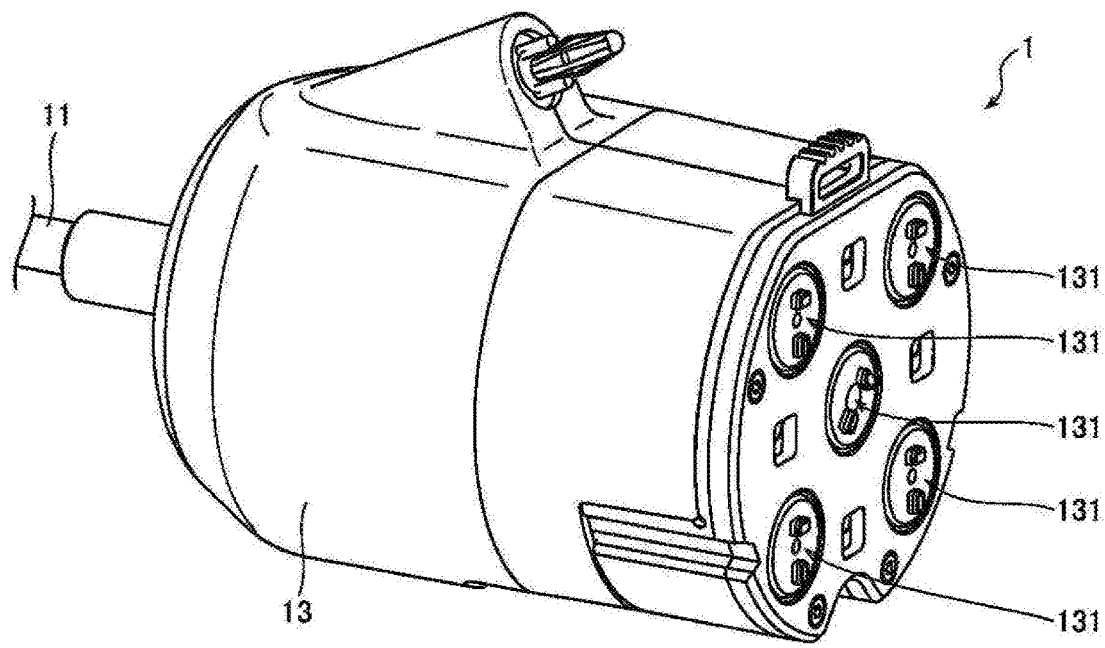
FIG. 8 is a diagram illustrating a perspective view of a main body of the surgical instrument of the surgical system according to an embodiment.

As shown in FIG. 8, the main body 13 of the surgical instrument 1 includes a plurality of driven members 131. Five driven members 131 are provided, for example. The driven members 131 are configured to be rotatable. Each of the driven members 131 is driven to rotate by an associated one of the plurality of motors 212 (see FIG. 6). When the driven member 131 is driven, the end effector 12 provided at the distal end is driven. Specifically, when the five driven members 131 are driven, one of the jaws 121 is driven to open or close in the directions of arrows A1; the other jaw 121 is driven to open or close in the directions of arrows A2; the pair of jaws 121 are driven to rotate in the directions of arrows A3; and the multi-articulated portion 122 is driven to bend in the directions of arrows A4 and the directions of arrows A5. The driving force of each of the five driven members 131 is transmitted to the end effector 12 via the wire or the torque transmission tube.

Figure 9A:
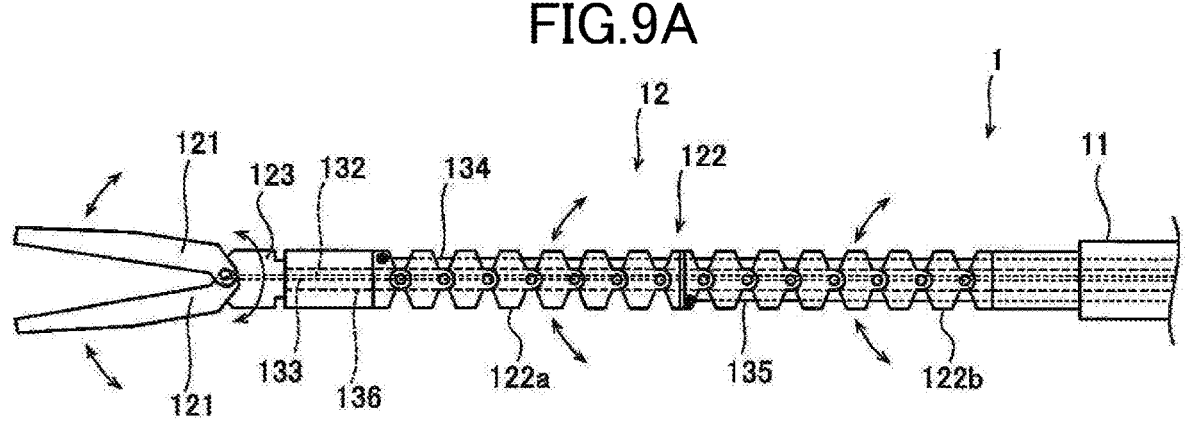
FIG. 9A is a diagram generally illustrating an end effector of the surgical instrument according to an embodiment.

As shown in FIG. 9A, the end effector 12 includes the pair of jaws 121, the multi-articulated portion 122, and a wrist 123. The pair of jaws 121 are provided at the distal end of the end effector 12. The pair of jaws 121 are configured to be openable and closable independently of each other. One end of the wrist 123 is connected to the pair of jaws 121. The wrist 123 is rotatable about a rotation axis, together with the pair of jaws 121 connected thereto. The multi-articulated portion 122 is in the form of a bendable joint. The multi-articulated portion 122 includes a plurality of parts arranged in a row, and a pin for connecting each adjacent pair of the parts. The multi-articulated portion 122 is configured to bend when the parts rotate about the pin. The multi-articulated portion 122 includes a first multi-articulated portion 122a and a second multi-articulated portion 122b. The first and second multi-articulated portions 122a and 122b are configured to be bendable independently of each other.

Figure 9B:
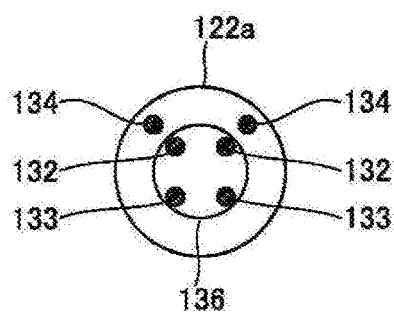
FIG. 9B is a diagram generally illustrating a cross-sectional view of a first multi-articulated portion of the end effector.
Figure 9C:
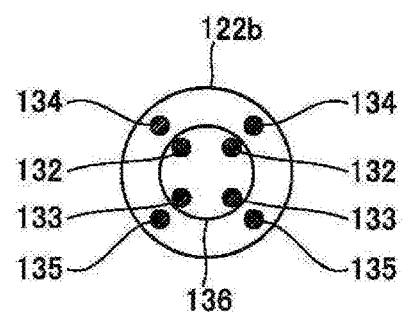
FIG. 9C is a diagram generally illustrating a cross-sectional view of a second multi-articulated portion of the end effector.

As shown in FIGS. 9A to 9C, the surgical instrument 1 includes wires 132, 133, 134, and 135 for driving the end effector 12, and a torque transmission tube 136. The wires 132, 133, 134, and 135 and the torque transmission tube 136 pass through the hollow flexible shaft 11 and are connected to the end effector 12 to allow transmission of the driving force of the main body 13 to the end effector 12. Each of the wires 132, 133, 134, and 135 is arranged so as to go around the end effector 12, and both ends thereof are wound around the driven member 131. In addition, each wire engages with the end effector 12 at an intermediate portion thereof. Thus, the wires 132, 133, 134, and 135 are pulled in or fed out along with the rotation of the driven members 131, so that the end effector 12 coupled to the wires 132, 133, 134, and 135 is driven. In FIG. 9A, the wires 132, 133, 134, and 135 are shown only partially for the sake of easy understanding.

The wire 132 is provided for driving one of the jaws 121 of the end effector 12 to open or close. The wire 133 is provided for driving the other jaw 121 of the end effector 12 to open or close. The wires 132 and 133 are arranged inside the torque transmission tube 136.

The wire 134 is provided for driving the first multi-articulated portion 122a of the end effector 12 to bend. The wire 135 is provided for driving the second multi-articulated portion 122b of the end effector 12 to bend. The wires 134 and 135 are arranged outside the torque transmission tube 136 and inside the flexible shaft 11 or the multi-articulated portion 122.

The torque transmission tube 136 is provided for driving the wrist 123 to rotate. The torque transmission tube 136 is arranged to pass through the hollow flexible shaft 11. The torque transmission tube 136 is connected to the wrist 123 of the end effector 12 at one end, and to the main body 13 at the other end. The torque transmission tube 136 has flexibility. That is, the torque transmission tube 136 is configured to be flexibly bendable (to be able to curve).

(Variations)

The one or more embodiments disclosed above are meant to be illustrative in all respects and should not be construed to be limiting in any manner. The scope of the invention is defined not by the above-described one or more embodiments, but by the scope of claims, and includes all modifications (variations) within equivalent meaning and scope to those of the claims.

For example, in the one or more embodiments described above, the surgical system includes the four surgical instruments, but this is a non-limiting example. In an embodiment, the surgical system may include five or more surgical instruments.

In the one or more embodiments described above, one of the plurality of surgical instruments is an endoscope, but this is a non-limiting example. In an embodiment, the plurality of surgical instruments do not necessarily include the endoscope, and two or more of the plurality of surgical instruments may be the endoscopes.

In the one or more embodiments described above, the support device movably supports the support mechanism with seven degrees of freedom, but this is a non-limiting example. In an embodiment, the support device may movably support the support mechanism with six or less, or eight or more degrees of freedom.

The invention claimed is:

1. A surgical system, comprising:
a first surgical instrument including a first flexible shaft and a first end effector;
a second surgical instrument including a second flexible shaft and a second end effector;
a third surgical instrument including a third flexible shaft and a third end effector;
a fourth surgical instrument including a fourth flexible shaft and a fourth end effector;
an insertion tube that holds the first flexible shaft, the second flexible shaft, the third flexible shaft, and the fourth flexible shaft, to be inserted into a body of a patient from one end of the insertion tube; and
a support device, wherein
the support device includes:
a first support including a first holder which holds a first driving section, the first driving section supporting the first surgical instrument and configured to drive the first surgical instrument;
a second support provided independently of the first support and including a second holder which holds a second driving section, the second driving section supporting the second surgical instrument and configured to drive the second surgical instrument;
a third support provided independently of the first support and the second support and including a third holder which holds a third driving section, the third driving section supporting the third surgical instrument and configured to drive the third surgical instrument;
a fourth support provided independently of the first support, the second support, and the third support and including a fourth holder which holds a fourth driving section, the fourth driving section supporting the fourth surgical instrument and configured to drive the fourth surgical instrument;
a support mechanism supporting the first, second, third, and fourth holders at regular intervals in a circumferential direction about a center line and configured to integrally move the first, second, third, and fourth holders supported at the regular intervals so as to integrally move the first, second, third, and fourth surgical instruments supported by the first, second, third, and fourth driving sections supported by the first, second, third, and fourth holders; and
an insertion tube holder connected to the support mechanism and holding the insertion tube, wherein the insertion tube holder includes one or more joints to adjust a position and orientation of the insertion tube with respect to the support mechanism.

2. The surgical system of claim 1, wherein the support device includes a translation mechanism that translates the support mechanism along the center line so as to collectively translate the first support, the second support, the third support and the fourth support along the center line.

3. The surgical system of claim 1, wherein the support device includes an angle change mechanism that rotates the support mechanism to collectively change angles of the first support, the second support, the third support, and the fourth support relative to a horizontal plane.

4. The surgical system of claim 1, wherein the first surgical instrument includes a first main body to which the first flexible shaft is attached; the second surgical instrument includes a second main body to which the second flexible shaft is attached; the third surgical instrument includes a third main body to which the third flexible shaft is attached; and the fourth surgical instrument includes a fourth main body to which the fourth flexible shaft is attached, wherein
the first main body is attached to the first driving section;
the second main body is attached to the second driving section;
the third main body is attached to the third driving section; and
the fourth main body is attached to the fourth driving section.

5. The surgical system of claim 4, wherein the first support is configured to translate the first holder in a longitudinal direction of the first surgical instrument,
the second support is configured to translate the second holder in a longitudinal direction of the second surgical instrument,
the third support is configured to translate the third holder in a longitudinal direction of the third surgical instrument, and
the fourth support is configured to translate the fourth holder in a longitudinal direction of the fourth surgical instrument.

6. The surgical system of claim 5, wherein the first holder is configured to rotate the first driving section about a first rotation axis parallel to the longitudinal direction of the first surgical instrument,
the second holder is configured to rotate the second driving section about a second rotation axis parallel to the longitudinal direction of the second surgical instrument,
the third holder is configured to rotate the third driving section about a third rotation axis parallel to the longitudinal direction of the third surgical instrument, and
the fourth holder is configured to rotate the fourth driving section about a fourth rotation axis parallel to the longitudinal direction of the fourth surgical instrument.

7. The surgical system of claim 4, wherein the first main body is configured to be attachable to and detachable from the first driving section; the second main body is configured to be attachable to and detachable from the second driving section; the third main body is configured to be attachable to and detachable from the third driving section; and the fourth main body is configured to be attachable to and detachable from the fourth driving section.

8. The surgical system of claim 4, wherein the first main body is configured to be attachable to and detachable from the first driving section via a first drape adapter; the second main body is configured to be attachable to and detachable from the second driving section via a second drape adapter; the third main body is configured to be attachable to and detachable from the third driving section via a third drape adapter; and the fourth main body is configured to be attachable to and detachable from the fourth driving section via a fourth drape adapter.

9. The surgical system of claim 1, wherein the insertion tube has a first end and a second end, and the insertion tube is configured to allow the first end effector, the second end effector, the third end effector, and the fourth end effector to be inserted into the insertion tube from the first end and introduced into the body of the patient from the second end.

10. The surgical system of claim 1, wherein the support device includes a vertical movement mechanism that moves the support mechanism in a vertical direction so as to collectively move the first support, the second support, the third support and the fourth support in the vertical direction, and a horizontal movement mechanism that moves the support mechanism in a horizontal direction so as to collectively move the first support, the second support, the third support and the fourth support in the horizontal direction.

11. The surgical system of claim 1, wherein the fourth surgical instrument is a flexible endoscope having a camera as the fourth end effector.

12. The surgical system of claim 1, wherein each of the first end effector, the second end effector, the third end effector, and the fourth end effector includes a bendable multi-articulated portion.

13. A support device for supporting first to fourth surgical instruments, the support device comprising:
  a first support including a first holder which holds a first driving section, the first driving section supporting the first surgical instrument including a first flexible shaft and a first end effector and configured to drive the first surgical instrument;
  a second support including a second holder which holds a second driving section, the second driving section supporting the second surgical instrument including a second flexible shaft and a second end effector and configured to drive the second surgical instrument;
  a third support including a third holder which holds a third driving section, the third driving section supporting the third surgical instrument including a third flexible shaft and a third end effector and configured to drive the third surgical instrument;
  a fourth support including a fourth holder which holds a fourth driving section, the fourth driving section supporting the fourth surgical instrument including a fourth flexible shaft and a fourth end effector and configured to drive the fourth surgical instrument;
  a support mechanism supporting the first, second, third, and fourth holders at regular intervals in a circumferential direction about a center line and configured to integrally move the first, second, third, and fourth holders supported at the regular intervals so as to integrally move the first, second, third, and fourth surgical instruments supported by the first, second, third, and fourth driving sections supported by the first, second, third, and fourth holders; and
  an insertion tube holder connected to the support mechanism and holding an insertion tube to hold the first to fourth flexible shafts, wherein the insertion tube holder includes one or more joints to adjust a position and orientation of the insertion tube with respect to the support mechanism.

14. The support device of claim 13, wherein the support device includes a translation mechanism that translates the support mechanism along the center line so as to collectively translate the first support, the second support, the third support and the fourth support along the center line.

15. The support device of claim 13, wherein the support device includes an angle change mechanism that rotates the support mechanism to collectively change angles of the first support, the second support, the third support, and the fourth support relative to a horizontal plane.

16. The support device of claim 13, wherein the first surgical instrument includes a first main body to which the first flexible shaft is attached; the second surgical instrument includes a second main body to which the second flexible shaft is attached; the third surgical instrument includes a third main body to which the third flexible shaft is attached; and the fourth surgical instrument comprising a flexible endoscope includes a fourth main body to which the fourth flexible shaft is attached.

17. The support device of claim 16, wherein the first support, the second support, the third support, and the fourth support are configured to translate the first holder, the second holder, the third holder, and the fourth holder, respectively.

18. The support device of claim 16, wherein the first main body is configured to be attachable to and detachable from the first driving section via a first drape adapter; the second main body is configured to be attachable to and detachable from the second driving section via a second drape adapter; the third main body is configured to be attachable to and detachable from the third driving section via a third drape adapter; and the fourth main body is configured to be attachable to and detachable from the fourth driving section via a fourth drape adapter.

* * * * *